United States Patent [19]

Dannecker et al.

[11] Patent Number: 6,162,425
[45] Date of Patent: Dec. 19, 2000

[54] SATURATED, ALKYL-SUBSTITUTED N-MERCAPTOACETYL HETEROCYCLIC COMPOUNDS AND COMPOSITIONS AND METHODS FOR PERMANENT SHAPING OF HAIR BASED ON SAME AND PROCESSES FOR MAKING SAME

[75] Inventors: Beate Dannecker, Darmstadt; Guenter Lang, Reinheim; Wolfgang Hanefeld; Heiko Walther, both of Marburg/Lahn, all of Germany

[73] Assignee: Wella Aktiengesellschaft, Darmstadt, Germany

[21] Appl. No.: 09/118,277

[22] Filed: Jul. 17, 1998

[30] Foreign Application Priority Data

Jul. 25, 1997 [DE] Germany ............... 197 32 079

[51] Int. Cl.⁷ .................................................. A61K 7/09
[52] U.S. Cl. ............................ 424/72; 548/535; 514/19; 514/315; 424/71
[58] Field of Search .................. 562/557; 548/535; 514/19, 315; 424/71, 72

[56] References Cited

U.S. PATENT DOCUMENTS 4,105,776  8/1978  Ondetti ..................... 424/274
4,107,330  8/1978  Sheffner .................... 424/317

FOREIGN PATENT DOCUMENTS 0 455 457 A2  11/1991  European Pat. Off. .
WO 91/10421   7/1991   WIPO .

*Primary Examiner*—Christopher S. F. Low
*Assistant Examiner*—David Lukton
*Attorney, Agent, or Firm*—Michael J. Striker

[57] ABSTRACT

The composition for permanent shaping of hair contains, as keratin-reducing agent, a compound of the formula (I):

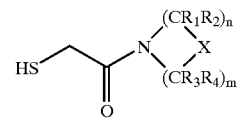

(I)

or a salt thereof, wherein $R_1$, $R_2$, $R_3$ and $R_4$ each represent, independently of each other, H, a straight or branched chain alkyl or hydroxy alkyl group, with 1 to 3 carbon atoms or a carboxyl group, with the proviso that at least one of the $R_1$, $R_2$, $R_3$ and $R_4$ groups is not H, n and m are whole numbers from 1 to 3 and X is a bivalent group —O—, —$CR_5R_6$— or —$NR_7$—, in which $R_5$, $R_6$ and $R_7$ are each, independently of each other, H or straight chain or branched chain alkyl groups or hydroxyalkyl groups with 1 to 3 carbon atoms or carboxyl groups. New mercaptoacetamide compounds and methods of making them are also described. The composition for permanent shaping provides a safe and uniform shaping of hair without allergic and sensitizing reactions; it has a skin and hair safe pH range of 6.5 to 9.5.

8 Claims, No Drawings

SATURATED, ALKYL-SUBSTITUTED N-MERCAPTOACETYL HETEROCYCLIC COMPOUNDS AND COMPOSITIONS AND METHODS FOR PERMANENT SHAPING OF HAIR BASED ON SAME AND PROCESSES FOR MAKING SAME

BACKGROUND OF THE INVENTION

The present invention relates to new mercaptoacetamide compounds, compositions and methods for permanent hair shaping that are based on these new mercaptoacetamide compounds or their salts as keratin-reducing agents and methods for making these new mercaptoacetamide compounds.

The known classical method for performing permanent hair shaping is based on two treatment steps: in the first step the cystine-disulfide-bridges of the hair keratin are opened by action of a composition containing a reducing agent. Then the hair is put into the desired shape. In a second step the cystine-disulfide-bridges are again closed using a fixing composition, i.e. a composition containing an oxidizing agent.

Thioglycolic acid, e.g. as an ammonium or monoethanolamine salt, is used as classical permanent wave reducing agent, as disclosed in the pioneering work in German Patents 948 186 and 972 424. Additional common reducing agents include inorganic sulfite, 2-mercaptopropionic acid (thiolactic acid), 3-mercaptopropionic acid, certain mercaptocarboxylic acid esters, cysteine and derivatives of these compounds.

All these compositions however have a series of disadvantages. Alkaline adjusted preparations based on mercaptocarboxylic acids, in spite of sufficient action, produce hair damage which manifests itself for example in increasing hair strand breaks. Furthermore these compositions load the scalp skin in an undesirable manner.

Finally the unpleasant smell of the reducing agent used requires an intensive perfuming of the product. Several of these problems however can be solved by using 2-mercaptopropionic acid (thiolactic acid). Generally thiolactic acid is characterized by a weaker shaping action than most of the other thioglycolic acids.

Mercaptocaroxylic acid esters which have hair shaping action even at reduced pH values, are unsatisfactory in regard to their skin compatiblity and their risk of sensitization. Instead of mercaptocarboxylic acid ester mercaptoacetamide compounds, such as thioglycolic acid amide or alkyl or hydroxyalkyl substituted amides, have also been used. Compositions of this type are disclosed in International Patent WO-A-91/10421 and European Patent EP-A-0 455 457. These materials have, like the carboxylic acid esters, highly effective shaping power, also at low pH values, however they are criticized even more than the esters in regard to their sensitizing action.

SUMMARY OF THE INVENTION

It has now been surprisingly found that the above-described disadvantages may be avoided using the mercaptoacetamide compounds of the formula (I) and that they have an even stronger shaping action than thiolactic acid.

According to the invention, the composition for permanent hair shaping contains, as keratin-reducing agent, a compound of the formula (I):

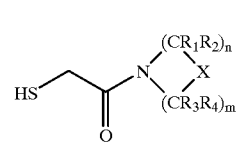

or a salt thereof, wherein $R_1$, $R_2$, $R_3$ and $R_4$ each represent, independently of each other, H, a straight or branched chain alkyl or hydroxy alkyl group with 1 to 3 carbons atoms or a carboxyl group, with the proviso that at least one of the $R_1$, $R_2$, $R_3$ and $R_4$ groups is not H, n and m are whole numbers from 1 to 3 and X is a bivalent group —O—, —$CR_5R_6$— or —$NR_7$—, in which $R_5$, $R_6$ and $R_7$ are each, independently of each other, H or straight chain or branched chain alkyl groups or hydroxyalkyl groups with 1 to 3 carbon atoms or carboxyl groups.

Preferred compounds of formula (I) are those, in which the $R_1$, $R_2$, $R_3$ and $R_4$ groups are H, $CH_3$, $CH_2CH_3$, $CH_2OH$, $CH_2CH_2OH$ or COOH, with the proviso that three of the $R_1$, $R_2$, $R_3$ and $R_4$ groups are H.

The compounds of the following formulae I' or I" are particularly preferred as compounds of formula I:

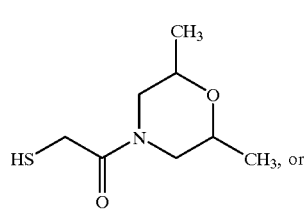

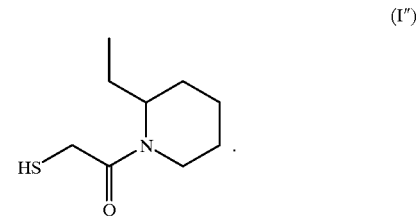

As salts of the mercaptoacetamide compounds of formula (I) suitable in the compositions of the invention all physiologically compatible salts, especially the hydrochloride, the sulfate, the phosphate, the lactate, the citrate and the acetate are suitable.

The mercaptoacetamide compounds of formula (I) according to the invention are used in the ready-to-use composition for permanent shaping of hair according to the invention in amounts of from 3 to 28% by weight, preferably 5 to 21% by weight. The mercaptoacetamide compounds can also be used in additional embodiments of the invention in mixture with each other or with other known thiol compounds, such as thioglycolic acids, thiolactic acids, cysteine, cysteamine, their salts or alkyl or acylcysteamines or sulfites.

The ready-to-use hair shaping compositions generally have a pH value of 3 to 9.5, preferably from 6.5 to 9.5, especially preferably from 6.5 to 8.5. The preferred pH range of the acid hair shaping compositions is from 3.5 to 5.5. Agents for adjustment of these pH values include especially ammonia or soda lye (sodium hydroxide), and also water-soluble physiologically compatible salts of organic and inorganic bases, such as e.g. ammonium hydrogen carbonate.

The hair shaping compositions can be packaged or marketed as a one or also a two component product. This composition can be present in the form of an aqueous solution or an aqueous emulsion and also in thickened form on an aqueous basis, especially as a cream, gel, foam or paste.

Understandably the hair shaping composition of the invention can contain conventional and known cosmetic additive ingredients, for example thickeners, such as bentonite, fatty acids, starches, polyacrylic acids and their derivatives, cellulose derivatives, alginates, petrolatum (Vaseline®), paraffin oil; wetting agents or emulsifiers from the classes of anionic, cationic, amphoteric or nonionic surface-active substances, for example fatty alcohol sulfates, fatty alcohol ether sulfates, alkyl sulfonates, alkylbenzene sulfates, quaternary ammonium salts, alkylbetaines, ethoxylated alkylphenols, fatty acid alkanol amides or ethoxylated fatty acids; additionally turbidity-inducing agents, such as polyethylene glycol esters; alcohols, such as ethanol, propanol, isopropanol, 1,2- or 1,3-propanediol, 1,2-, 1,3- or 1,4-butanediol, 1,2-, 1,3-, 1,4- or 1,5-pentanediol, polyols or their methyl or ethyl ethers, such as diethylene glycol monomethyl ether and glycerol; sugars, such a D-glucose; solvating agents, stabilizers, buffer substances, perfume oils, dye compounds and hair conditioning and hair care-giving ingredients, such as cationic polymers, lanolin derivatives, cholesterol, pantothenic acids and betaine.

The above-mentioned ingredients are used in the usual amounts according to their purpose, for example the wetting agents and emulsifiers are used in total concentrations of 0.2 to 30 percent by weight; the alcohols, in total concentrations of from 0.1 to 20 percent by weight; the turbidity-inducing agents, perfume oils and dye compounds, in total concentrations of from 0.01 to 1 percent by weight; the buffer substances, in total amounts of from 0.1 to 10 percent by weight; the sugars, solvating agents, stabilizers and hair conditioning and hair care-giving agents, in total amounts of from 0.1 to 5 percent by weight respectively, while the thickeners and solvating agents can be contained in total amounts of from 0.5 to 20 percent by weight.

Furthermore the compositions according to the invention can also contain a so-called swelling and penetrating agent, such as, e.g., dipropylene glycol monomethyl ether, 2-pyrrolidone or imidazolidin-2-one, in an amount of 1 to 30 percent by weight and dithiocompounds, such as dithiodiglycolic acid, dithiolactic acid, the disulfides of the above-mentioned compounds or the respective salts, to avoid over-curling of the hair.

By changing the pH and, if necessary heating, a composition according to the invention can be provided that is universally suitable for any type of hair structure. This composition provides an elastic, permanent and uniform shaping of the hair from the hair roots to the hair tips, without allergic or sensitizing reactions.

The present invention also concerns a method for permanent shaping of the hair, in which one puts the hair in the desired shape or hair-do before or after treatment, treats the hair with a shaping agent, rinses the hair with water, then performs an oxidative after-treatment, rinses the hair with water again, puts the hair in a water-water if necessary and then dries it. This method is characterized by the use of the above-described treatment composition for the shaping of the hair.

In a preferred embodiment of the method according to the invention the hair is first washed with a shampoo and after that rinsed with water. Subsequently the hand-towel-dried hair is divided into individual strands and wound on curlers with a diameter of 5 to 30 millimeters, preferably 5 to 15 millimeters. Then the hair is treated with a sufficient quantity of the hair shaping composition of the invention, preferably 60 to 120 grams.

After an acting time sufficient for the permanent shaping of the hair, which amounts to from 5 to 30 minutes (10 to 30 minutes without heating, 5 to 20 minutes with heating) depending on the hair condition, the pH value and the shaping effectiveness of the hair shaping composition, the hair is rinsed with water and then oxidatively after-treated (fixed). The after-treatment composition, is used, according the hair quantity, preferably in an amount of 80 to 100 grams.

Any arbitrary after-treatment composition suitable for this type of treatment may be used for the oxidative after-treatment with the hair wound on the curlers or after the curlers are removed. For example, oxidizing agents used in this type of after-treatment composition include potassium and sodium bromate, sodium perborate, urea peroxide and hydrogen peroxide. The concentration of the oxidizing agent differs according to the application time (usually 5 to 15 minutes) and the application temperature. Normally from 0.5 to 10 percent by weight of the oxidizing agent is present in the ready-to-use aqueous after-treatment composition. The composition for oxidative after-treatment understandably can include additional ingredients, for example wetting agents, care-giving materials, such as cationic polymers, weak acids, buffer substances or peroxide stabilizers, and can be in the form of an aqueous solution, an emulsion and in thickened form on an aqueous basis, especially a cream, gel or paste. These additional conventional ingredients can, for example, be present in the after-treatment composition in amounts of from 0.1 to 10 percent by weight.

The subject matter of the invention also includes the following new mercaptoacetamide compounds of the formula (II),

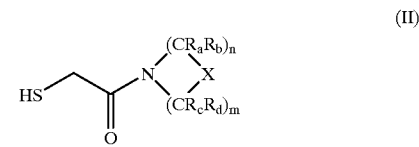

(II)

and their salts, wherein $R_a$, $R_b$, $R_c$ and $R_d$ each represent, independently of each other, H, a straight or branched chain alkyl or hydroxy alkyl group, with 1 to 3 carbons atoms with the proviso that at least one of the $R_a$, $R_b$, $R_c$ and $R_d$ groups is not H, n and m are whole numbers from 1 to 3 and X is a bivalent group —O—, —$CR_5R_6$— or —$NR_7$—, in which $R_5$, $R_6$ and $R_7$ are each, independently of each other, H or straight chain or branched chain alkyl groups or hydroxyalkyl groups with 1 to 3 carbon atoms or carboxyl groups.

Furthermore the subject matter of the invention includes a process for making the mercaptoamide compounds of formula (I) and (II), in which a respective secondary amine at a temperature of not over 30° C. reacts with methylthioglycolate. This is described in more detail in production example 1 according to method A and production examples 2 to 4.

The following examples should illustrate the subject matter of the invention without limiting the subject matter to the details of these examples.

EXAMPLES

Example 1

Manufacture of Mercaptoacetamide According to Method A 2 mol of a selected secondary amine are placed in a 500 ml three-necked flask. 1 mol of methyl thioglcolate are added dropwise with cooling by means of a water bath so that the temperature does not exceed 30° C. The reaction mixture is thoroughly rinsed with argon and then stirred until the methyl thioglycolate is reacted quantitatively (control by thin layer chromatography in Merck DC Alufoil 5×10 cm; silica gel 60 F 254).

The reaction mixture is acidified with 36% hydrochloride acid with ice cooling and extracted exhaustively with ethyl acetate. The solvent is distilled in vacua by rotary evaporator, the residue is brought to a pH of 7 by addition of soda lye (sodium hydroxide) and shaken again with ethyl acetate. The combined fractions are dried over sodium sulfate and concentrated further. The residue present is distilled to form as pure a product as possible by means of a molecular distillation apparatus with a maximum pressure of 0.01 Torr. This method is decisive for making as pure a product as possible with a good yield. It is possible to avoid impurities formed by incompletely reacted fission products formed by thermolysis or hydrolysis only by careful distillations because of the sensitive properties of these products.

Manufacture of Mercaptoacetamide According to Method B

A mole of the respective secondary amine is dissolved in 500 ml of water (cyclic amino acids in 500 ml of 1 N NaOH) in a 1 l three-necked flask and cooled in an ice bath at 0° C. The solution is mixed with 250 ml 2N NaOH and one mol of chloroacetyl chloride is added dropwise so that the temperature does not exceed 5° C. The reaction mixture is vigorously stirred for three hours at room temperature. After that the mixture is mixed with a mole of potassium ethyl xanthogenate and stirred for an additional twelve hours at room temperature. The mixture is acidified with 36% hydrochloride acid until a yellow oil precipitates. This oil is separated and dissolved in a mixture of 500 ml 25% ammonia and 250 ml ethanol. It is stirred for an hour at room temperature. After that the ethanol is distilled away in vacuo in a rotary evaporator, and the residue shaken with ethyl acetate. The aqueous phase is cautiously acidified and again extracted with ethyl acetate. The solvent in distilled off in vacuo in a rotary evaporator, the residue is purified by distillation (see method A) or recrystallized from ethyl acetate.

TABLE I

Compounds Prepared according to the Processes of the Invention

| Mercaptoacetamide/Amino ingredient | Yield % | Elemental Analysis calculated/found | HPLC (FP) | Boiling Point ° C. | WSN pH = 7 | WSN pH = 8 | WSN pH = 9 |
|---|---|---|---|---|---|---|---|
| 1) 2'-ethyl-N,N-pentamethylene mercaptoacetamide/2-ethyl piperidine | 18 | C: 57.71, H: 9.15 N: 7.48, S: 17.12 C: 57.28, H: 8.94 N: 7.85, S: 16.66 | 97.18 | 90 at 0.01 torr | 59 | 61 | 84 |
| 2) 2'-methyl-N,N-pentamethylene mercaptoacetamide/2-methyl piperidine | 16 | C: 55.45, H: 8.73 N: 8.08, S: 18.50 C: 54.82, H 8.73 N: 7.98, S: 18.39 | 98.92 | 103 at 0.015 torr | 76 | 87 | 97 |
| 3) 3'-methyl-N,N-pentamethylene mercaptoacetamide/3-methyl piperidine | 70 | C: 55.45, H: 8.73 N: 8.08, S: 18.50 C: 55.35, H: 8.29 N: 8.11, S: 18.27 | 96.06 | 110 at 0.03 torr | 71 | 72 | 97 |
| 4) 4'-methyl-N,N-pentamethylene mercaptoacetamide/4-methyl piperidine | 44 | C: 55.45, H: 8.73 N: 8.08, S: 18.50 C: 55.40, H: 8.65 N: 8.00, S: 18.48 | 98.78 | 110 at 0.02 torr | 63 | 82 | 94 |
| 5) 2,6-dimethyl-4-mercaptoacetyl-morpholine/2,6-dimethylmorpholine | 51 | C: 50.77, H: 7.99 N: 7.40, S: 16.94 C: 50.60, H: 7.85 N: 7.60, S: 16.76 | 97.45 | 97 at 0.02 torr | 78 | 86 | 94 |
| 6) N-mercaptoacetylproline/ Proline | 44 | C: 44.43, H: 5.86 N: 7.40, S: 16.94 C: 44.10, H: 5.87 N: 7.10, S: 17.02 | 98.99 | Fp: 128 | 51 | 73 | 74 |
| Thiolacticacid for comparison | | | | | 57 | 50 | 70 |

Example 2

Process for Making 2,6-Dimethyl-4-mercaptoacetylmorpholine 230.26 g (2 mol) 2,6-dimentylmorpholine are introduced into a 500 ml three-necked flask. 106.24 g of methyl thioglycolate are added slowly dropwise so that the temperature does not exceed 30° C. The reaction mixture is rinsed with argon and stirred for 2 days at room temperature.

The mixture is acidified with 36% hydrochloric acid (pH 2 to 4) with ice cooling and extracted exhaustively with ethyl acetate. The solvent is distilled away, the residue is brought to pH=7 by addition of soda lye (sodium hydroxide) and again shaken with ethyl acetate. The combined fractions are dried over sodium sulfate and concentrated. The residue present is distilled to form a pure product by means of a molecular distillation apparatus with a maximum pressure of 0.01 Torr. The yield amounts to 96.52 g(51%).

Analysis:

a) $^1$H-NMR(CDCl$_3$):
  δ(ppm)=
   4.38+3.66 (m,1H,CH),
   4.04+3.96 (m,1H,CH),
   3.6+3.1+2.8+2.3 (m,4H,2× N—CH$_2$),
   3.3 (s,2H,HS—CH$_2$—CO),
   2.05 (s,1H,HS),
   1.1 (qa,6H,2× CH$_3$).

b) $^{13}$C-NMR(CDCl$_3$):
δ(ppm)=
169.0+168.3 (—C=O),
71.8+66.8 (O—CH),
71.6+65.7 (O—CH),
51.8+51.26 (N—CH$_2$—),
47.47+46.8 (N—CH$_2$—),
26.03+25.82 (HS—CH$_2$—),
18.74+17.52 (CH$_3$).

c) MS(70 eV, EI, RT)
M/z(%)=(M+)=
189(7.05),
174(12.8), 142(40.37), 131(45.13),
84(19.5), 70(61.4), 43(100)

d) Thiotitration: 99.30% e) Elemental analysis: C$_8$H$_{15}$NO$_2$S (MW: 189.27 g/mol)
Calculated: C:50.77; H:7.99; N:7.40; S:16.94;
Found: C:50.60; H:7.85; N:7.60; S:16.76.

f) IR(NaCl-glass)
2974–2874s (CH$_2$)
2545w (SH)
1641s (N—N-disubstituted amide)

g) HPLC:
The HPLC gives a result of 97.44 percent for the Compound.
(column: C 18 5U, 250 mm×4.6 mm; eluent, acetonitrile; buffer {4 g KH$_2$PO$_4$+0.8 g octane sulfonic acid-Na salt: +2 ml H$_3$PO$_4$}, flow rate, 0.5 ml/min; wavelength 222 nm=25:75 } g) pKs: 7.58(H$_2$O )

h) UV-max: 228 nm(acetonitrile: buffer=25:75)

j) Boiling Point: 97° C./0.02 Torr

Example 3

Process for Making 3'-Methyl-N,N-pentamethylene mercaptoacetamide 198 g (2 mol) 3-methylpiperidine is placed in a 500 ml three-necked flask. 106.24 g of methyl thioglycolate are slowly added dropwise so that the temperature does not exceed 30° C. The reaction mixture is rinsed thoroughly rinsed with argon and /stirred for 2 days at room temperature.

The mixture is acidified with 36% hydrochloric acid with ice cooling and extracted exhaustively with ethyl acetate. The solvent is distilled off in vacuo with a rotary evaporator. The residue is brought to pH=7.0 by addition of soda lye and shaken again with ethyl acetate. The combined fractions are dried over sodium sulfate and concentrated. The resulting residue is distilled by a molecular distillation apparatus under high vacuum with at most 0.01 Torr to obtain a pure product. The yield amounted to 121 g (70%).
Analysis:

a) $^1$H-NMR(CDCl$_3$):
δ(ppm)=
4.4+3.69+2.7 (3× m, 3H, N(CH$_2$)2),
3.04+2.31 (m, 1H, N(CH$_2$)2),
3.35 (d, 2H, HS—CH$_2$—CO)
2.1 (s,1H,HS),
1.8 (m,1H,(CH$_{2equat.}$—CH—CH$_3$))
1.6 (m,3H,CH—+N—CH$_2$—CH$_2$),
1.1 (m,1H,(CH$_{2axial}$—)$^2$—CH—CH$_3$))
0.92 (d,3H,CH$_3$).

b) $^{13}$C-NMR(CDCl$_3$):
δ(ppm)=
167.98 (C=O),
53.75+49.5+46.8+42.7 (2× N—CH$_2$),
32.81 (CH),
32.75+30.7 (N—CH$_2$—CH$_2$),
26.17 (HS—CH$_2$),
25.7 +24.6 (N—CH$_2$—CH$_2$),
18.8 (CH$_3$).

c) MS(70 eV, EI, RT)
M/z(%)=(M+)=
173(6.15),
141(13.77),140(100),126(19.74),
98(14.50),83(12.80), 69(5.33),55(33.38)

d) Thiotitration: 96.44% e) Elemental analysis: C$_8$H$_{15}$NOS (MW: 173.27 g/mol)
Calculated: C:55.45; H:8.73; N:8.08; S:18.50;
Found: C:55.35; H:8.29; N:8.11; S:18.27.

f) IR(NaCl-glass)
2929–2853s (CH$_2$)
2546w (SH)
1639s (N—N-disubstituted amide)

g) HPLC:
The HPLC gives a result of 96.06 percent for the Compound.
(column: C 18 5U, 250 mm×4.6 mm; eluent, acetonitrile; buffer {4 g KH$_2$PO$_4$+0.8 g octane sulfonic acid-Na salt+2 ml H$_3$PO$_4$}, flow rate, 0.5 ml/min; wavelength 200 nm=25:75} g) pKs: 8.16(H$_2$O )

h) UV-max: 233 nm(acetonitrile: buffer=25:75)

j) Boiling Point: 110° C./0.03 Torr

Example 4

Process for Making 4'-Methyl-N,N-pentamethylene mercaptoacetamide 198 g (2 mol) 4-methylpiperidine is placed in a 500 ml three-necked flask. 106.24 g of methyl thioglycolate are slowly added dropwise so that the temperature does not exceed 30° C. The reaction mixture is rinsed thoroughly rinsed with argon and stirred for 2 days at room temperature.

The mixture is acidified with 36% hydrochloric acid with ice cooling (pH=2 to 4) and extracted exhaustively with ethyl acetate. The solvent is distilled off in vacuo with a rotary evaporator. The residue is brought to pH=7.0 by addition of soda lye (sodium hydroxide) and shaken again with ethyl acetate. The combined fractions are dried over sodium sulfate and concentrated. The resulting residue is distilled by a molecular distillation apparatus under high vacuum with at most 0.01 Torr to obtain a pure product. The yield amounted to 76 g (44%).
Analysis:

a) $^1$H-NMR(CDCl$_3$):
δ(ppm)=
4.52+3.75+3.07+2.61(4× m, 4H, N(CH$_2$)2),
3.22 (d, 2H, HS—CH$_2$—CO)
2.1 (bulged, 1H, HS),
1.7 (m,3H,C$_H$—+(CH$_{2equat}$)$_2$—CH—CH$_3$)),
1.1 (m,2H,(CH$_{2axial}$—)$_2$—CH—CH$_3$))
0.95 (d,3H,CH$_3$).

b) $^{13}$C-NMR(CDCl$_3$):
δ(ppm)=
168.13 (C=O),
46.66+42.65 (2× N—CH$_2$),
34.51 (N—CH$_2$—CH$_2$),
33.61 (N—CH$_2$—CH$_2$), 30.94 (HS—$CH_2$),
26.25 (CH),
21.62 ($CH_3$).

c) MS(70 eV, EI, RT)
M/z(%)=(M+)=
173(13.12),
141(24.82),140(100),126(34.91),
98(19.19),83(26.90),69(11.57),55(67.70)

d) Thiotitration: 97.22% e) Elemental analysis: $C_8H_{15}NOS$ (MW: 173.27 g/mol)
Calculated: C:55.45; H:8.73; N:8.08; S:18.50;
Found: C:55.40; H:8.65; N:8.00; S:18.48.

f) IR(NaCl-glass)
2999–2858s ($CH_2$)
2541w (SH)
1636s (N—N-disubstituted amide)

g) HPLC:
The HPLC gives a result of 98.78 percent for the Compound.
(column: C 18 5U, 250 mm×4.6 mm; eluent, acetonitrile; buffer {4 g $KH_2PO_4$+0.8 g octane sulfonic acid-Na salt+2 ml $H_3PO_4$}, flow rate, 0.5 ml/min; wavelength 200 nm=25:75} g) pKs: 8.14($H_2O$)

h) UV-max: 232.4 nm(acetonitrile: buffer=25:75)

j) Boiling Point: 110° C./0.02 Torr

Example 5

Process for Making 2'-Methyl-N,N-pentamethylene mercaptoacetamide 99 g (1 mol) 2-methylpiperidine is dissolved in 500 ml of water placed in a 1 l three-necked flask and cooled in an ice-water bath to 0° C. The solution is mixed with 250 ml of 2N NaOH and 112 g (1 mol) chloroacetyl chloride is added dropwise so that the temperature does not exceed 5° C. The reaction mixture is vigorously stirred for three hours at room temperature. After that the mixture is mixed with 160 g (1 mol) of potassium ethyl xanthogenate and stirred an additional twelve hours. The mixture is acidified with 36% hydrochloric acid until a yellow oil precipitates. This oil is separated and dissolved in a mixture of 500 mol of 25% ammonia and 250 ml ethanol. It is stirred for an hour at room temperature. The ethanol solvent is distilled off in vacuo with a rotary evaporator and the residue is shaken with ethyl acetate. The aqueous phase is acidified with 36% hydrochloric acid (pH 2 to 4) with ice cooling and exhaustively extracted with ethyl acetate. The solvent is distilled off in vacuo with a rotary evaporator, the residue is brought to pH=7.0 by addition of soda lye (sodium hydroxide) and shaken again with ethyl acetate. The combined fractions are dried over sodium sulfate and concentrated. The resulting residue is distilled by a molecular distillation apparatus under high vacuum with at most 0.01 Torr to obtain a pure product. The yield amounted to 27 g (16%).

Analysis:

a) $^1$H-NMR($CDCl_3$):
δ(ppm)=
4.4+4.0+3.6+3.1+2.6 (3× m, 3H,CH+N—$CH_2$),
3.3 (d, 2H, HS—$CH_2$—CO)
2.2 (s,1H,HS),
1.6–1.4 (m,6H, N—$CH_2$—$CH_2$—$CH_2$—$CH_2$),
1.6 (m,3H,(CH—+N—$CH_2$—$CH_2$)
1.2–1.1 (2× d, 3H,$CH_3$).

b) $^{13}$C-NMR($CDCl_3$):
δ(ppm)=
168.30 (C=O),
49.3+44.4+41.6+36.9 (N—$CH_2$+N—CH),
30.99+29.73 (N—$CH_2$—$CH_2$—$CH_2$),
26.75+26.20 (HS—$CH_2$),
26.40+25.45 (N—$CH_2$—$CH_2$),
19.28 (N—$CH_2$—$CH_2$—$CH_2$),
15.46+15.24 ($CH_3$).

c) MS(70 eV, EI, RT)
M/z(%)=(M+)=
173(1.78),
141(100), 126(22.23), 98(16.30),
84(40.6), 55(28)

d) Thiotitration: 99.01% e) Elemental analysis: $C_8H_{15}NOS$ (MW: 173.27 g/mol)
Calculated: C:55.45; H:8.73; N:8.08; S:18.50;
Found: C:54.82; H:8.69; N:7.98; S:18.39.

f) IR(NaCl-glass)
2937–2854s ($CH_2$)
2539w (SH)
1635s (N—N—disubstituted amide)

g) HPLC:
The HPLC gives a result of 98.92 percent for the Compound.
(column: C 18 5U, 250 mm×4.6 mm; eluent, acetonitrile; buffer {4 g $KH_2PO_4$+0.8 g octane sulfonic acid-Na salt+2 ml $H_3PO_4$}, flow rate, 0.5 ml/min; wavelength 200 nm=25:75} g) pKs: 8.21($H_2O$ )

h) UV-max: 222.4 nm(acetonitrile: buffer=25:75)

j) Boiling Point: 103° C./0.15 Torr

Example 6

Process for Making 2'-Ethyl-N,N-pentamethylene mercaptoacetamide 113 g (1 mol) 2-ethylpiperidine is dissolved in 500 ml of water placed in a 1 l three-necked flask and cooled in an ice-water bath to 0° C. The solution is mixed with 250 ml of 2N NaOH and 112 g (1 mol) chloroacetyl chloride is added dropwise so that the temperature does not exceed 5° C. The reaction mixture is vigorously stirred for three hours at room temperature. After that the mixture is mixed with 160 g (1 mol) of potassium ethyl xanthogenate and stirred an additional twelve hours. The mixture is acidified with 36% hydrochloric acid until a yellow oil precipitates. This oil is separated and dissolved in a mixture of 500 ml of 25% ammonia and 250 ml ethanol. It is stirred for an hour at room temperature. The ethanol is distilled off in vacuo with a rotary evaporator and the residue is shaken with ethyl acetate. The aqueous phase is acidified with 36% hydrochloric acid (pH 2 to 4) with ice cooling and exhaustively extracted with ethyl acetate. The solvent is distilled off in vacuo with a rotary evaporator, the residue is brought to pH=7.0 by addition of soda lye (sodium hydroxide) and shaken again with ethyl acetate. The combined fractions are dried over sodium sulfate and concentrated. The resulting residue is distilled by a molecular distillation apparatus under high vacuum with at most 0.01 Torr to obtain a pure product. The yield amounted to 34 g (18%).

Analysis:

a) $^1$H-NMR($CDCl_3$):
δ(ppm)=
4.6+4.4+3.7+3.5+3.1+2.6 (6× m,3H,N—CH+N—$CH_2$), 3.3 (d, 2H, HS—CH$_2$—CO)
2.1 (bulged, 1H, HS),
1.7–1.3 (m, 8H, all residual CH$_2$ groups),
0.95 (t,3H,CH$_3$).

b) $^{13}$C-NMR(CDCl$_3$):
δ(ppm)=
168.61 (C=O),
55.5+50.0 (N—CH)
41.9+37.1 (N—CH$_2$),
28.7+27.6 (N—CH$_2$—CH$_2$),
26.70+26.27 (HS—CH$_2$),
26.51+25.36 (N—CH—CH$_2$—CH$_2$),
23.1+22.3 (N—CH—CH$_2$—CH$_2$),
18.9 (CH$_2$—CH$_2$)
10.9+10.6 (CH$_3$).

c) MS(70 eV, EI, RT)
M/z(%)=(M+)=
187(4.37),
158(29.3), 154(70.4), 140(11.80),
84(100), 55(21.56)

d) Thiotitration: 98.54% e) Elemental analysis: C$_9$H$_{17}$NOS (MW: 187.30 g/mol)
Calculated: C:57.71; H:9.15 N:7.48; S:17.12;
Found: C:57.28; H:8.94; N:7.85; S:16.66.

f) IR(NaCl-glass)
2936–2869s (CH$_2$)
2538w (SH)
1636s (N—N-disubstituted amide)

g) HPLC:
The HPLC gives a result of 97.18 percent for the Compound.
(column: C 18 5U, 250 mm×4.6 mm; eluent, acetonitrile; buffer {4 g KH$_2$PO$_4$+0.8 g octane sulfonic acid-Na salt+2 ml H$_3$PO$_4$}, flow rate, 0.5 ml/min; wavelength 200 nm=25:75} g) pKs: 8.354(H$_2$O)

h) UV-max: 229 nm(acetonitrile: buffer=25:75)

j) Boiling Point: 90° C./0.1 Torr

Example 7

Process for Making N-Mercaptoacetylproline 115 g (1 mol) proline is dissolved in 500 ml of water placed in a 1 l three-necked flask and cooled in an ice-water bath to 0° C. The solution is mixed with 250 ml of 2N NaOH and 112 g (1 mol) chloroacetyl chloride is added dropwise so that the temperature does not exceed 5° C. The reaction mixture is vigorously stirred for three hours at room temperature. After that the mixture is mixed with 160 g (1 mol) of potassium ethyl xanthogenate and stirred an additional twelve hours. The mixture is acidified with 36% hydrochloric acid until a yellow oil precipitates. This oil is separated and dissolved in a mixture of 500 ml of 25% ammonia and 250 ml ethanol. It is stirred for an hour at room temperature. The ethanol is distilled off in vacuo with a rotary evaporator and the residue is shaken with ethyl acetate. The aqueous phase is acidified with 36% hydrochloric acid (pH 2 to 4) with ice cooling and exhaustively extracted with ethyl acetate. The solvent is distilled off in vacuo with a rotary evaporator, the residue is brought to pH=7.0 by addition of soda lye (sodium hydroxide) and shaken again with ethyl acetate. The combined fractions are dried over sodium sulfate and concentrated. The resulting residue is distilled by a molecular distillation apparatus under high vacuum with at most 0.01 Torr to obtain a pure product. The yield amounted to 83 g (44%).

Analysis:

a) $^1$H-NMR(CDCl$_3$):
δ(ppm)=
4.6+4.4 (m,1H, N—CH),
3.7 (m, 2H, N—CH$_2$)
3.3 (s, 2H, HS—CH$_2$—CO), 2.2–2.0 (m, 4H, CH$_2$—CH$_2$).

b) $^{13}$C-NMR(CDCl$_3$):
δ(ppm)=
175.3+175.0 (COOH),
171.7+171.3 (CON),
61.0+60.6 (N—CH),
49 (N—CH$_2$),
32.12+30.40 (N—CH—CH$_2$),
27.39 (HS—CH$_2$)
25.68+23.48 (N—CH$_2$—CH$_2$).

c) MS(70 eV, EI, RT)
M/z(%)=(M+)=
189(31.39),
171(25.5), 156(84.4), 114(64.43),
112(100), 70(97.7)

d) Thiotitration: 95.75% e) Elemental analysis: C$_7$H$_{11}$NO$_3$S (MW: 189.23 g/mol)
Calculated: C:44.43; H:5.86; N:7.40; S:16.94;
Found: C:44.10; H:5.87; N:7.10; S:17.02.

f) IR(NaCl-glass)
3000–2200s (CH$_2$+OH)
2538w (SH)
1713 (COOH)
1587s (N—N-disubstituted amide)

g) HPLC:
The HPLC gives a result of 98.99 percent for the Compound.
(column: C 18 5U, 250 mm×4.6 mm; eluent, acetonitrile; buffer {4 g KH$_2$PO$_4$+0.8 g octane sulfonic acid-Na salt+2 ml H$_3$PO$_4$}, flow rate, 0.5 ml/min; wavelength 200 nm=25:75} g) pKs: 8.70(H$_2$O)

h) UV-max: 220 nm(acetonitrile: buffer=25:75)

j) FP: 128° C.

Example 8

Comparison of Permanent Wave Effectiveness

The permanent wave effectiveness of permanent wave solutions containing N-Mercaptoacetamides and having pH values of 7, 8 and 9 was compared with solutions containing glycerol monothioglycolate as comparative control. For that purpose counted, bleached, and thus damaged, moist hair strands of Central European hair (containing about 100 hairs) having a length of 16.5 centimeters were wound on standard spiral curlers and, after conditioning in a climate controlled room (temperature, 20° C.; humidity, 65%), were treated with reducing agent solutions containing 87 mmol/100 g of the reducing agent at the respective pH values. The ratio of the fixing composition to the permanent wave composition was 1:1.2 (1 g hair:1.2 ml of the permanent wave composition). The acting time was 20 minutes and the acting temperature was 50° C. Subsequently the hair was fixed with a hydrogen peroxide-containing fixing composition, dried and, after removal from the curlers, suspended for four hours in water (water bath temperature: 40° C.).

The wave stability is calculated according to the following formula:

Wave stability in % $=100\times\{(L_o-L_t)/(L_o-L_1)\}$ wherein $L_o$=the total length of the not shaped extended strands (i.e. 16.5 cm);

$L_t$=the length of the uncurled suspended strands are 240 minutes; and $L_1$=the length of the shaped curled strands (this amounts to 35 mm for a curler linear diameter of 3 mm).

For comparison strands were also treated with a suitable glycerol monothioglycolate adjusted to a pH=9. The normalized stabilities (WSN) given in Table I in reference to the standard solution (pH=9) whose wave stability was set to 100 percent.

Table I shows that the wave effectiveness of the thioacetamides according to the invention at pH=7, 8 and 9 is greater than that of thiolactic acid.

Example 9

Permanent Wave Composition for Dyed Hair

| | |
|---|---|
| 16.5 g | 2,6-dimethyl-4-mercaptoacetyl-morpholine |
| 0.4 g | ammonia (25% aqueous solution) for pH adjustment |
| 2.0 g | ammonium hydrogen carbonate |
| 5.0 g | 1,2-pentanediol |
| 1.0 g | isooctyl phenol, ethoxylated with 10 Mol ethylene oxide |
| 1.0 g | poly(dimethyldiallyl ammonium chloride) |
| 0.6 g | cocoamidopropyl betaine |
| 0.3 g | perfume oil |
| 0.1 g | vinyl pyrrolidone/styrene mixed polymerizate (Antara ® 430 of GAF Corp., New York, NY, USA) |
| 73.1 g | water |
| 100.0 g | |

The pH value of this composition is 7.3.

Hair damaged by a dyeing treatment is washed with a shampoo, rubbed and wound on curlers with a diameter of 8 millimeters. Subsequently the above-described hair shaping composition is uniformly distributed on the curled hair. Then the hair is covered with a plastic bonnet and heated for 10 minutes under a drying hood at a temperature of 45° C. Subsequently the covering is removed, the hair rinsed with water and oxidatively after-treated with 100 g of a 3 percent aqueous hydrogen peroxide solution. After removing the curler the hair is rinsed again with water, put in a water wave and then dried. A uniform, elastic and permanent shaping of hair is obtained as a result of this treatment.

Example 10

Permanent Wave Composition for Normal Hair

| | |
|---|---|
| 22.0 g | N-mercaptoacetylproline |
| 8.9 g | ammonia (25% aqueous solution) for pH adjustment |
| 5.0 g | ammonium hydrogen carbonate |
| 5.0 g | 1,3-butanediol |
| 2.0 g | diethyleneglycol monoethyl ether |
| 2.0 g | urea |
| 2.4 g | monoethanol amine |
| 1.5 g | isooctyl phenol, ethoxylated with 10 Mol ethylene oxide |
| 0.5 g | poly(dimethyldiallyl ammonium chloride) |
| 0.5 g | perfume oil, turbidity-inducing agent |
| 0.1 g | vinyl pyrrolidone/styrene mixed polymerizate (Antara ® 430 of GAF Corp., New York, NY, USA) |
| 50.1 g | water |
| 100.0 g | |

The pH value of this composition is 8.4.

Normal undamaged hair is washed with a shampoo, rubbed with a hand towel and wound on curlers with a diameter of 6 millimeters. Subsequently the above-described hair shaping composition is uniformly distributed on the curled hair. After an acting time of 15 minutes, the hair rinsed with water and oxidatively after-treated with 80 g of a 3 percent aqueous hydrogen peroxide solution. After removing the curlers, the hair is rinsed again with water, put in a water wave and then dried. The hair treated in this way has a uniform and vivacious curl.

Example 11

Permanent Wave Composition for Normal Hair

| | |
|---|---|
| 20.0 g | 2'-methyl-N,N-pentamethylene mercapto-acetamide |
| 8.9 g | ammonia (25% aqueous solution) for pH adjustment |
| 5.0 g | ammonium hydrogen carbonate |
| 5.0 g | isopropanol |
| 5.0 g | 1,2-propanediol |
| 2.0 g | D-glucose |
| 2.4 g | ammonia |
| 1.5 g | isooctyl phenol, ethoxylated with 10 Mol ethylene oxide |
| 0.5 g | poly(dimethyldiallyl ammonium chloride) |
| 0.5 g | perfume oil |
| 0.1 g | vinyl pyrrolidone/styrene mixed polymerizate (Antara ® 430 of GAF Corp., New York, NY, USA) |
| 49.1 g | water |
| 100.0 g | |

The pH value of this composition is 8.3

Normal undamaged hair is washed with a shampoo, rubbed with a hand towel and wound on curlers with a diameter of 6 millimeters. Subsequently the above-described hair shaping composition is uniformly distributed on the curled hair. After an acting time of 15 to 25 minutes, the hair rinsed with water and oxidatively after-treated with 80 g of a 3 percent aqueous hydrogen peroxide solution. After removing the curlers, the hair is rinsed again with water, put in a water wave and then dried. The hair treated in this way has a uniform and vivacious curl.

Example 12

Permanent Wave Composition for Normal Hair

| | | |
|---|---|---|
| 7.4 g | 2'-ethyl-N,N-pentamethylene mercapto-acetamide | |
| 2.0 g | 2-thiolactic acid | |
| 12.0 g | ammonium thioglycolate, 70% | |
| 8.9 g | ammonia (25% aqueous solution) for pH adjustment | |
| 5.0 g | ammonium hydrogen carbonate | |
| 5.0 g | isopropanol | |
| 5.0 g | 1,2-propanediol | |
| 2.0 g | D-glucose | |
| 2.4 g | ammonia | |
| 1.5 g | isooctyl phenol, ethoxylated with 10 Mol ethylene oxide | |
| 0.5 g | poly(dimethyldiallyl ammonium chloride) | |
| 0.5 g | perfume oil | |
| 0.1 g | vinyl pyrrolidone/styrene mixed polymerizate (Antara ® 430 of GAF Corp., New York, NY, USA) | |
| 50.5 g | water | |
| 100.0 g | | |

The pH value of this composition is 8.5.

Normal undamaged hair is washed with a shampoo, rubbed with a hand towel and wound on curlers with a diameter of 6 millimeters. Subsequently the above-described hair shaping composition is uniformly distributed on the curled hair. After an acting time of 15 to 25 minutes, the hair rinsed with water and oxidatively after-treated with 80 g of a 3 percent aqueous hydrogen peroxide solution. After removing the curlers, the hair is rinsed again with water, put in a water wave and then dried. The hair treated in this way has a uniform and vivacious curl.

Example 13

Permanent Wave Composition for Normal Hair

| | | |
|---|---|---|
| 6.9 g | 3'-methyl-N,N-pentamethylene mercapto-acetamide | |
| 2.0 g | cysteine hydrochloride H2O | |
| 12.0 g | ammonium thioglycolate, 70% | |
| 8.9 g | ammonia (25% aqueous solution) for pH adjustment | |
| 5.0 g | ammonium hydrogen carbonate | |
| 8.0 g | isopropanol | |
| 2.0 g | 1,2-propanediol | |
| 0.5 g | diethylene glycol monomethyl ether | |
| 2.4 g | ammonia | |
| 1.5 g | isooctyl phenol, ethoxylated with 10 Mol ethylene oxide | |
| 0.5 g | poly(dimethyldiallyl ammonium chloride) | |
| 0.5 g | perfume oil | |
| 0.1 g | vinyl pyrrolidone/styrene mixed polymerizate (Antara ® 430 of GAF Corp., New York, NY, USA) | |
| 49.5 g | water | |
| 100.0 g | | |

The pH value of this composition is 8.5.

Normal undamaged hair is washed with a shampoo, rubbed with a hand towel and wound on curlers with a diameter of 6 millimeters. Subsequently the above-described hair shaping composition is uniformly distributed on the curled hair. After an acting time of 15 to 25 minutes, the hair rinsed with water and oxidatively after-treated with 80 g of a 3 percent aqueous hydrogen peroxide solution. After removing the curlers, the hair is rinsed again with water, put in a water wave and then dried. The hair treated in this way has a uniform and vivacious curl.

The disclosure in German Patent Application 197 32 079.1-44 of Jul. 25, 1997 is incorporated herein by reference. This German Patent Application describes the invention described hereinabove and claimed in the claims appended herein in below and provides the basis for a claim of priority for the instant invention under 35 U.S.C. 119.

While the invention has been illustrated and described as embodied in saturated, alkyl-substituted N-Mercaptoacetyl heterocyclic compounds, processes for making them and compositions and methods for permanent hair shaping based on them, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:

1. An aqueous composition for permanent shaping of hair having a pH of from 3 to 9.5 and comprising water;

from 3 to 28% by weight of a compound of the formula (I), as keratin-reducing agent:

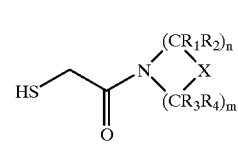

(I)

or a salt thereof, wherein $R_1$, $R_2$, $R_3$ and $R_4$ are each independently selected from the group consisting of H, alkyl groups having 1 to 3 carbon atoms, hydroxyalkyl groups having 1 to 3 carbon atoms and a carboxyl group, wherein at least one of said $R_1$, $R_2$, $R_3$ and $R_4$ is not said H;

n is 1, 2 or 3;

m is 1, 2 or 3; and

X is a bivalent group —O—, —C($R_5$)$R_6$— or —NR$_7$—, where said $R_5$, $R_6$ and $R_7$ are each independently selected from the group consisting of H, alkyl groups having 1 to 3 carbon atoms, hydroxyalkyl groups having 1 to 3 carbon atoms and a carboxyl group;

from 0.1 to 10 percent by weight of buffer substances;

from 0.2 to 30 percent by weight of at least one wetting agent or emulsifier;

from 0.5 to 20 percent by weight of at least one thickener;

from 0.1 to 20 percent by weight of at least one alcohol;

from 0.01 to 1 percent by weight of at least one member selected from the group consisting of turbidity-inducing agents, perfume oils and dye compounds; and from 0.1 to 5 percent by weight of at least one ingredient selected from the group consisting of sugars, solvating agents, stabilizers and hair conditioning and hair care-giving agents.

2. The aqueous composition as defined in claim 1, wherein said $R_1$, $R_2$, $R_3$ and $R_4$ are, each independently of each other, selected from the group consisting of H, $CH_3$, $CH_2CH_3$, $CH_2OH$, $CH_2CH_2OH$ and COOH, wherein three of said $R_1$, $R_2$, $R_3$ and $R_4$ are each said H.

3. The aqueous composition as defined in claim 1, wherein said pH is from 3.5 to 5.5.

4. A mercaptoacetamide compound for permanent shaping of hair of the formula (II):

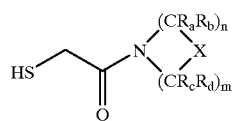
(II)

or a salt thereof, wherein $R_a$, $R_b$, $R_c$, and $R_d$ are each independently selected from the group consisting of H, alkyl groups having 1 to 3 carbon atoms and hydroxyalkyl groups having 1 to 3 carbon atoms, wherein at least one of said $R_a$, $R_b$, $R_c$ and $R_d$ is not said H;

n is 1, 2 or 3;

m is 1, 2 or 3; and

X is a bivalent group —O—, —C($R_5$)$R_6$— or —$NR_7$—, where said $R_5$, $R_6$ and $R_7$ are each independently selected from the group consisting of H, alkyl groups having 1 to 3 carbon atoms, hydroxyalkyl groups having 1 to 3 carbon atoms and a carboxyl group.

5. A compound for permanent shaping of hair which is 2'-methyl-N,N-pentamethylene mercaptoacetamide.

6. A compound for permanent shaping of hair which is 2'-ethyl-N,N-pentamethylene mercaptoacetamide.

7. A compound for permanent shaping of hair which is 3'-methyl-N,N-pentamethylene mercaptoacetamide.

8. A compound for permanent shaping of hair which is 2,6-dimethyl-4-mercaptoacetyl-morpholine.

* * * * *